US012691188B2

(12) United States Patent
Hayakawa et al.

(10) Patent No.: US 12,691,188 B2
(45) Date of Patent: Jul. 28, 2026

(54) METHOD OF STERILIZING DRINK FILLING APPARATUS AND DRINK FILLING APPARATUS

(71) Applicant: Dai Nippon Printing Co., Ltd., Tokyo (JP)

(72) Inventors: Atsushi Hayakawa, Tokyo (JP); Shuta Ito, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 1236 days.

(21) Appl. No.: 17/593,068

(22) PCT Filed: Apr. 13, 2020

(86) PCT No.: PCT/JP2020/016344
§ 371 (c)(1),
(2) Date: Sep. 8, 2021

(87) PCT Pub. No.: WO2020/213575
PCT Pub. Date: Oct. 22, 2020

(65) Prior Publication Data
US 2022/0226516 A1     Jul. 21, 2022

(30) Foreign Application Priority Data
Apr. 17, 2019     (JP) ................................. 2019-078831

(51) Int. Cl.
*A61L 2/07*          (2006.01)
*B08B 9/032*        (2006.01)

(52) U.S. Cl.
CPC .............. *A61L 2/07* (2013.01); *B08B 9/0325* (2013.01); *B08B 2230/01* (2013.01)

(58) Field of Classification Search
CPC ........ A61L 2/07; A61L 2/186; A61L 2202/11; A61L 2202/14; A61L 2/04; B08B 9/0325; B08B 2230/01; B08B 9/027; B67C 3/001
See application file for complete search history.

(56) References Cited

U.S. PATENT DOCUMENTS

2015/0291406 A1    10/2015  Hayakawa et al.
2016/0121376 A1*    5/2016  Hayakawa ............ B08B 9/0325
                                                                    422/3
2018/0280552 A1*   10/2018  Hanano .................. A23B 70/30

FOREIGN PATENT DOCUMENTS

JP        2000-153245 A       6/2000
JP        2007-022600 A       2/2007
(Continued)

OTHER PUBLICATIONS

International Search Report and Written Opinion (Application No. PCT/JP2020/016344) dated Jul. 7, 2020.

*Primary Examiner* — Brendan A Hensel
(74) *Attorney, Agent, or Firm* — Muncy, Geissler, Olds & Lowe, P.C.

(57) ABSTRACT

To reduce the time required to start a drink filling operation or the time interval between productions.
In a method of sterilizing a drink filling apparatus that includes drink supply piping that feeds a drink into a filling machine through a heating sterilization part, a heated liquid or heated steam is fed to the drink supply piping, temperatures of the drink supply piping at a plurality of positions are detected at predetermined time intervals, a lowest temperature is selected from the detected temperatures, an F value is calculated for the selected lowest temperature, the calculated F value is integrated, and a sterilization step is ended when the integrated F value reaches a target value.

6 Claims, 10 Drawing Sheets

(56)        References Cited

FOREIGN PATENT DOCUMENTS

| | | | | |
|---|---|---|---|---|
| JP | 2007-215893 | A | 8/2007 | |
| JP | 2007-331801 | A | 12/2007 | |
| JP | 2015-044593 | A | 3/2015 | |
| WO | 2014/103787 | A1 | 7/2014 | |
| WO | WO-2014208551 | A1 * | 12/2014 | .............. A61L 2/04 |

* cited by examiner

METHOD OF STERILIZING DRINK FILLING APPARATUS AND DRINK FILLING APPARATUS

TECHNICAL FIELD

The present invention relates to a method of sterilizing an apparatus that fills a container such as a PET bottle with a drink, and an apparatus that fills a container with a drink.

BACKGROUND ART

When an aseptic filling apparatus fills a container such as a bottle with a drink, not only does the drink itself have to be sterilized to be aseptic, but also the interior of drink supply piping including a surge tank, a liquid feeding pipe, and filling nozzles in the aseptic filling apparatus have to be cleaned and sterilized to be aseptic in advance.

Conventionally, with regard to the drink itself flowing in the drink filling path, the F value, which is a sterilization value, of the drink is measured, and it is checked based on the historical information on the F value whether or not the drink is sterilized to such an extent that the quality of the drink can be assured (see Patent Literature 4, for example).

With the drink supply piping of the aseptic filling apparatus, a CIP (Cleaning in Place) process and an SIP (Sterilizing in Place) process are performed regularly or each time the kind of drink is changed (see Patent Literatures 1, 2 and 3, for example).

CIP is performed by passing a cleaner containing water and an alkali agent such as caustic soda as an additive through a flow path from the pipe line of the drink filling path to the filing nozzles of the filling machine and then passing a cleaner containing water and an acid agent as an additive. CIP removes a residue of the previous drink in the drink filling path, for example (see Patent Literatures 1, 2 and 3, for example).

SIP is a process to sterilize the interior of the drink supply piping before the drink filling operation is started, and is performed by passing a heated steam or heated liquid through the drink filling path cleaned by CIP described above, for example. SIP sterilizes the interior of the drink filling path and makes it aseptic (see Patent Literature 3, for example).

SIP is performed by passing a heated steam or a heated liquid through the drink filling path. Conventionally, it is determined to end SIP when a predetermined time has elapsed since the temperature of a predetermined part of the interior of the drink supply piping of the drink filling path reached a predetermined temperature. However, in this way of ending SIP, the energy loss is high. Therefore, a plurality of temperature sensors are provided in the drink supply piping of the drink filling apparatus that includes the drink supply piping that feeds a drink into the filling machine through the heating sterilization part, F values are calculated from the temperatures detected by the temperature sensors, and SIP is ended when the minimum of the calculated F values reaches a target value (see Patent Literatures 5 and 6).

CITATION LIST

Patent Literature

Patent Literature 1: Japanese Patent Laid-Open No. 2007-331801
Patent Literature 2: Japanese Patent Laid-Open No. 2000-153245

Patent Literature 3: Japanese Patent Laid-Open No. 2007-22600
Patent Literature 4: Japanese Patent Laid-Open No. 2007-215893
Patent Literature 5: International Publication No. WO 2014/103787
Patent Literature 6: Japanese Patent Laid-Open No. 2015-044593

SUMMARY OF INVENTION

Technical Problem

Conventionally, the F value is strictly managed, because when sterilizing a drink or food by heating, the quality such as taste or feel of the drink or food varies with the heating duration.

However, drink supply piping of an aseptic filling apparatus is mainly made of metal such as stainless steel and does not change in quality compared with the drink, so that the F value is relatively roughly managed for the drink supply piping.

For example, the F value is 233 when heating continues for 30 minutes at 130° C., and it is empirically known that this value is adequate for the sterilization process for the drink supply piping. Therefore, the temperature is measured by temperature sensors disposed at different positions on the drink supply piping where the temperature is less likely to increase while passing a heated steam or heated liquid through the drink supply piping, a timer is activated when the temperature from each temperature sensor reaches 130° C., and the heating of the drink supply piping with the heated steam or heated liquid is ended when the timer counts to 30 minutes.

FIG. 11 is a graph showing a relationship between temperature and time of a method of heating drink supply piping. Specifically, the drink supply piping starts being heated by feeding steam or the like continuously for 30 minutes from the time when the lowest temperature of the temperatures measured by the temperature sensors at different positions in the drink supply piping reaches 130° C., the supply of the steam or the like is stopped when 30 minutes has elapsed, and aseptic cooling air or the like is then supplied to cool the interior of the drink supply piping. In FIG. 11, the temperature is raised to 135° C., in order to allow for a variation of the temperature for safety reasons. In FIG. 11, the sterilization conditions are that the temperature is 130° C. or higher for 30 minutes, and the area of the hatched part corresponds to the F value of 233. In actuality, however, the integrated part of the F value above 130° C. is ignored.

With the recent progress of energy conservation, the amount of thermal energy consumed for SIP has become a problem. In addition, the length of time required for SIP has also become a problem, from the viewpoint of the drink production efficiency. In view of this, it has become a common practice to provide the drink supply piping with a plurality of temperature sensors, calculate the F values from the temperatures detected by the temperature sensors, and end SIP when the minimum F value of the plurality of calculated F values reaches a target value.

However, calculating and integrating the F values for all the detected temperatures puts a heavy load on the computing apparatus, and the computing apparatus requires a relatively large amount of cost.

An object of the present invention is to provide a method of sterilizing a drink filling apparatus and a drink filling apparatus that do not impose a load on the computing apparatus and can manage SIP based on an F value with a relatively inexpensive computing apparatus when performing SIP in the drink filling apparatus.

Solution to Problem

A method of sterilizing a drink filling apparatus according to the present invention is a method of sterilizing a drink filling apparatus that includes drink supply piping that feeds a drink into a filling machine through a heating sterilization part, wherein a heated liquid or heated steam is passed through the drink supply piping, temperatures of the drink supply piping at a plurality of positions are detected at predetermined time intervals, a lowest temperature is selected from the detected temperatures, an F value is calculated for the selected lowest temperature, the calculated F value is integrated, and a sterilization step is ended when the integrated F value reaches a target value.

In the method of sterilizing a drink filling apparatus according to the present invention, preferably, an upstream-side feedback path is provided for an upstream-side piping section of the drink supply piping that passes through the heating sterilization part to form an upstream-side circulation path, the heated liquid or heated steam is passed through the upstream-side circulation path, temperatures of the upstream-side piping section at a plurality of positions are detected at predetermined time intervals, a lowest temperature is selected from the detected temperatures, an F value is calculated for the selected lowest temperature, the calculated F value is integrated, and a sterilization step of the upstream-side piping section is ended when the integrated F value reaches a target value.

In the method of sterilizing a drink filling apparatus according to the present invention, preferably, the heated liquid or heated steam is passed through a downstream-side piping section of the drink supply piping that extends from a point downstream of an upstream-side piping section of the drink supply piping that passes through the heating sterilization part to an interior of a filling machine via an aseptic surge tank and a filling machine tank, temperatures of the downstream-side piping section at a plurality of positions are detected at predetermined time intervals, a lowest temperature is selected from the detected temperatures, an F value is calculated for the selected lowest temperature, the calculated F value is integrated, and a sterilization step of the downstream-side piping section is ended when the integrated F value reaches a target value.

In the method of sterilizing a drink filling apparatus according to the present invention, preferably, the heated liquid or heated steam is passed through the aseptic surge tank of the downstream-side piping section, temperatures of the aseptic surge tank at a plurality of positions are detected at predetermined time intervals, a lowest temperature is selected from the detected temperatures, an F value is calculated for the selected lowest temperature, the calculated F value is integrated, and a sterilization step of the aseptic surge tank is ended when the integrated F value reaches a target value.

In the method of sterilizing a drink filling apparatus according to the present invention, preferably, the heated liquid or heated steam is passed through a filling piping section of the downstream-side piping section that extends to the interior of the filling machine via the filling machine tank, temperatures of the filling piping section at a plurality of positions are detected at predetermined time intervals, a lowest temperature is selected from the detected temperatures, an F value is calculated for the selected lowest temperature, the calculated F value is integrated, and a sterilization step of the filling piping section is ended when the integrated F value reaches a target value.

In the method of sterilizing a drink filling apparatus according to the present invention, preferably, the heated liquid or heated steam is passed through a carbonating piping section between the aseptic surge tank and the filling machine tank of the downstream-side piping section, the carbonating piping section including a carbonating unit and a carbonated drink surge tank, temperatures of the carbonating piping section at a plurality of positions are detected at predetermined time intervals, a lowest temperature is selected from the detected temperatures, an F value is calculated for the selected lowest temperature, the calculated F value is integrated, and a sterilization step of the carbonating piping section is ended when the integrated F value reaches a target value.

A method of sterilizing a drink filling apparatus according to the present invention is a method of sterilizing a drink filling apparatus that includes an aseptic water producing unit that supplies aseptic water into a filling part chamber that shields a filling part, wherein an aseptic water supply piping section that passes through the aseptic water producing unit is provided with an aseptic water feedback path to form an aseptic water circulation path, a heated liquid or heated steam is passed through the aseptic water circulation path, temperatures of the aseptic water supply piping section at a plurality of positions are detected at predetermined time intervals, a lowest temperature is selected from the detected temperatures, an F value is calculated for the selected lowest temperature, the calculated F value is integrated, and a sterilization step of the aseptic water supply piping section is ended when the integrated F value reaches a target value.

In the methods of sterilizing a drink filling apparatus according to the present invention, preferably, the F value is calculated according to the following formula:

$$F = \int_{t_0}^{t_1} 10^{(T-121.1)/10} dt \qquad \text{[Formula 1]}$$

Where T denotes an arbitrary sterilization temperature (° C.), $10^{(T-121.1)/10}$ represents a fatality rate at an arbitrary temperature T and corresponds to a heating duration (in minutes) at 121.1° C., which is a reference temperature, and 10 denotes a Z value (° C.).

A drink filling apparatus according to the present invention is a drink filling apparatus comprising drink supply piping that feeds a drink into a filling machine through a heating sterilization part, wherein the drink filling apparatus comprises temperature sensors that detect temperatures of the drink supply piping at a plurality of positions at predetermined time intervals, and a controller that instructs to pass a heated liquid or heated steam through the drink supply piping, to select a lowest temperature from the temperatures detected by the temperature sensors, to calculate an F value from the selected lowest temperature, to integrate the calculated F value, and to end a sterilization step when the integrated F value reaches a target value.

In the drink filling apparatus according to the present invention, preferably, an upstream-side feedback path is provided for an upstream-side piping section of the drink supply piping that passes through the heating sterilization part to form an upstream-side circulation path, and the drink filling apparatus comprises temperature sensors that detect temperatures of the upstream-side piping section at a plurality of positions at predetermined time intervals, and a controller that instructs to pass the heated liquid or heated steam through the upstream-side circulation path, to select a lowest temperature from the detected temperatures by the temperature sensors, to calculate an F value from the selected lowest temperature, to integrate the calculated F value, and to end a sterilization step of the upstream-side piping section when the integrated F value reaches a target value.

In the drink filling apparatus according to the present invention, preferably, the drink filling apparatus comprises temperature sensors that detect temperatures of a downstream-side piping section of the drink supply piping at a plurality of positions at predetermined time intervals, the downstream-side piping section extending from a point downstream of an upstream-side piping section of the drink supply piping that passes through the heating sterilization part to an interior of a filling machine via an aseptic surge tank and a filling machine tank, and a controller that instructs to pass the heated liquid or heated steam through the downstream-side piping section, to select a lowest temperature from the temperatures detected by the temperature sensors, to calculate an F value from the selected lowest temperature, to integrate the calculated F value, and to end a sterilization step of the downstream-side piping section when the integrated F value reaches a target value.

In the drink filling apparatus according to the present invention, preferably, the drink filling apparatus comprises temperature sensors that detect temperatures of the aseptic surge tank of the downstream-side piping section at a plurality of positions at predetermined time intervals, and a controller that instructs to pass the heated liquid or heated steam through the aseptic surge tank, to select a lowest temperature from the temperatures detected by the temperature sensors, to calculate an F value for the selected lowest temperature, to integrate the calculated F value, and to end a sterilization step of the aseptic surge tank when the integrated F value reaches a target value.

In the drink filling apparatus according to the present invention, preferably, the drink filling apparatus comprises temperature sensors that detect temperatures of a filling piping section of the downstream-side piping section at a plurality of positions at predetermined time intervals, the filling piping section extending to the interior of the filling machine via the filling machine tank, and a controller that instructs to pass the heated liquid or heated steam through the filling piping section, to select a lowest temperature from the temperatures detected by the temperature sensors, to calculate an F value for the selected lowest temperature, to integrate the calculated F value, and to end a sterilization step of the filling piping section when the integrated F value reaches a target value.

In the drink filling apparatus according to the present invention, preferably, the drink filling apparatus comprises temperature sensors that detect temperatures of a carbonating piping section at a plurality of positions at predetermined time intervals, the carbonating piping section being between the aseptic surge tank and the filling machine tank of the downstream-side piping section and including a carbonating unit and a carbonated drink surge tank, and a controller that instructs to pass the heated liquid or heated steam through the carbonating piping section, to select a lowest temperature from the temperatures detected by the temperature sensors, to calculate an F value for the selected lowest temperature, to integrate the calculated F value, and to end a sterilization step of the carbonating piping section when the integrated F value reaches a target value.

A drink filling apparatus according to the present invention is a drink filling apparatus comprising an aseptic water producing unit that supplies aseptic water into a filling part chamber that shields a filling part, wherein an aseptic water supply piping section that passes through the aseptic water producing unit is provided with an aseptic water feedback path to form an aseptic water circulation path, and the drink filling apparatus comprises temperature sensors that detect temperatures of the aseptic water supply piping section at a plurality of positions at predetermined time intervals, and a controller that instructs to pass a heated liquid or heated steam through the aseptic water circulation path, to select a lowest temperature from the temperatures detected by the temperature sensors, to calculate an F value for the selected lowest temperature, to integrate the calculated F value, and to end a sterilization step of the aseptic water supply piping section when the integrated F value reaches a target value.

Advantageous Effects of Invention

According to the present invention, for SIP of the drink supply piping and the aseptic water supply piping of the drink filling apparatus, the integration of the F value is started early, and the sterilization step is ended when the F value reaches a target value. Therefore, SIP of the drink supply piping and the aseptic water supply piping of the drink filling apparatus can be more precisely and quickly achieved than before. Therefore, the usage of the heated liquid and heated steam for the sterilization of the drink supply piping and the aseptic water supply piping can be reduced, the drink filling operation can be started earlier, the time intervals between productions when changing the kind of drink can be reduced, and thus the production efficiency can be improved. Furthermore, since the lowest temperature is selected from the temperatures detected by a plurality of temperature sensors provided on the drink supply piping and the aseptic water supply piping, the F value is calculated from the selected temperature, the calculated F value is integrated, and SIP is ended when the integrated F value reaches a target value, the number of calculations of the F value can be reduced, and therefore, the cost of the computing apparatus can be substantially reduced compared with the case where the F value is calculated for all the detected temperatures.

BRIEF DESCRIPTION OF DRAWINGS

FIG. 2 is a block diagram showing drink supply piping in the drink filling apparatus according to the embodiment of the present invention, in which an upstream-side piping section from a heating sterilization part to an inlet of an aseptic surge tank is being subjected to SIP.

FIG. 3 is a block diagram showing the drink supply piping in the drink filling apparatus according to the embodiment of the present invention, in which a downstream-side piping section from the aseptic surge tank to filling nozzles is being subjected to SIP.

FIG. 5 is a block diagram showing the drink supply piping in the drink filling apparatus according to the embodiment of the present invention, in which a carbonating piping section from a carbonating unit to a carbonated drink surge tank is being subjected to SIP.

FIG. 6 is a block diagram showing the drink supply piping in the drink filling apparatus according to the embodiment of the present invention, in which a filling piping section from a filling machine tank to the filling nozzles is being subjected to SIP.

FIG. 7 is a block diagram showing an aseptic water supply piping section passing through an aseptic water producing unit in the drink filling apparatus according to the embodiment of the present invention being subjected to SIP.

FIG. 8 is a block diagram showing the drink filling apparatus according to the embodiment of the present invention producing a bottled non-carbonated drink product.

FIG. 9 is a block diagram showing the drink filling apparatus according to the embodiment of the present invention producing a bottled carbonated drink product.

DESCRIPTION OF EMBODIMENT

In the following, an embodiment of the present invention will be described with reference to the drawings.

First, a configuration of a drink filling apparatus will be described, and a sterilization method for the apparatus will then be described.

Figure 1:
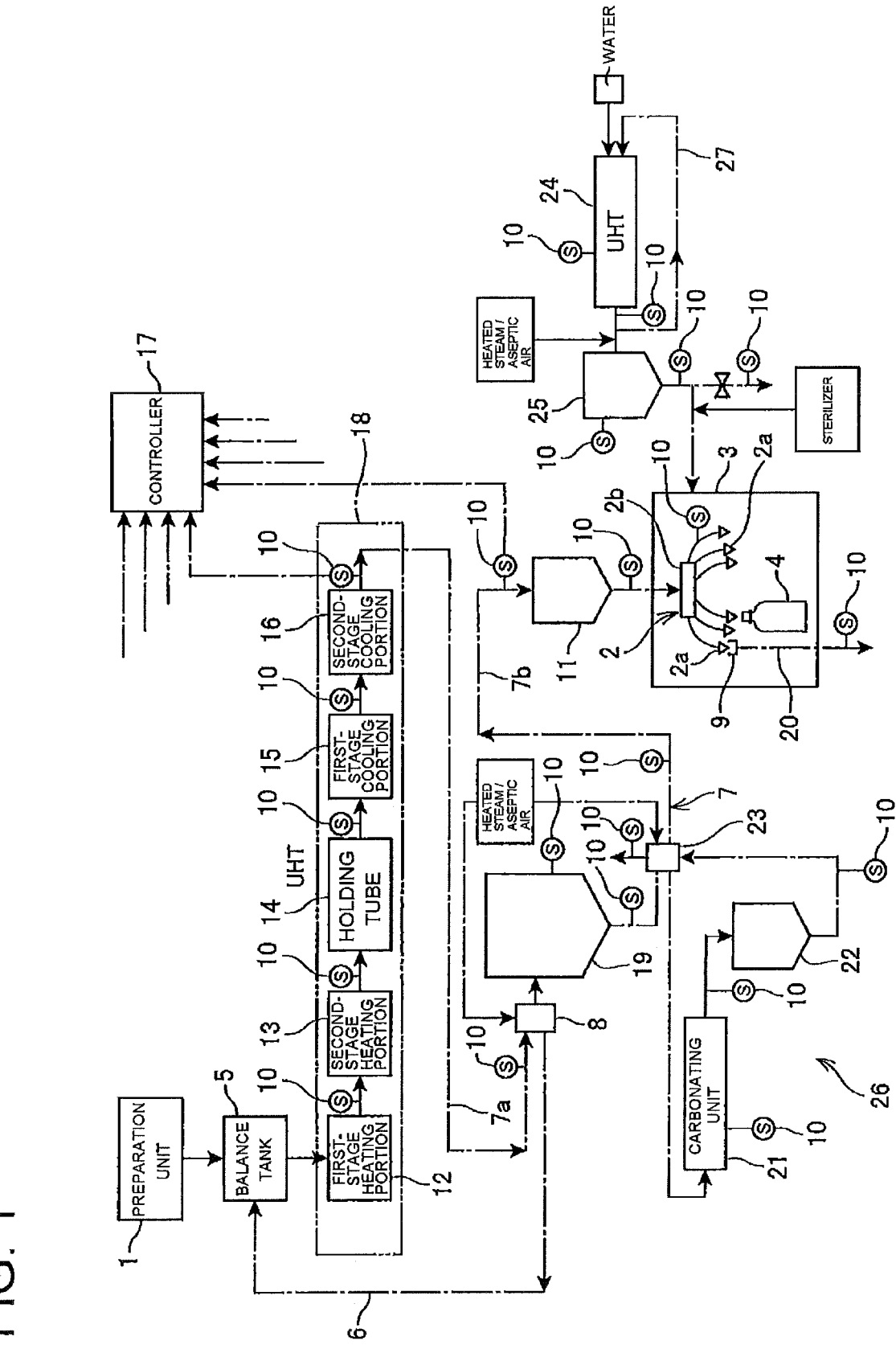
FIG. 1 a block diagram showing a drink filling apparatus according to an embodiment of the present invention.

As shown in FIG. 1, the drink filling apparatus includes a preparation unit 1 for a drink and a filling machine 2 that fills a bottle 4 with the drink. The preparation unit 1 and filling nozzles 2a in the filling machine 2 are coupled to each other by drink supply piping 7. A filling part including the filling machine 2 is surrounded by a filling part chamber 3.

The preparation unit 1 prepares a drink such as tea or fruit juice by mixing ingredients in desired proportions. The preparation unit 1 is a well-known device and therefore will not be described in detail herein.

The filling machine 2 includes a large number of filling nozzles 2a arranged around a wheel (not shown), which rotates at high speed in a horizontal plane. As the wheel rotates, the filling nozzles 2a rotate, and the drink is metered from the filling nozzles 2a to bottles 4 traveling below the filling nozzles 2a at a velocity adjusted to the circumferential velocity of the wheel. The filling machine 2 is also a well-known machine and therefore will not be described in detail herein.

In the drink filling apparatus, along the path of the drink supply piping 7 from the preparation unit 1 to the filling machine 2, a balance tank 5, a heating sterilization part (hereinafter, referred to as UHT: Ultra High-temperature) 18, a manifold valve 8, an aseptic surge tank 19, and a filling machine tank 11 are disposed in this order from the upstream side to the downstream side of the flow of the drink.

When a carbonated drink is produced by carbonating a drink, the drink supply piping 7 of the drink filling apparatus includes a cooling unit (not shown), a carbonating unit 21, and a carbonated drink surge tank 22. The cooling unit, the carbonating unit 21 and the carbonated drink surge tank 22 are provided between the aseptic surge tank 19 and the filling machine tank 11 in this order from the upstream to the downstream, and a carbonated drink manifold valve 23 is provided to pass the carbonated drink to the drink supply piping.

In the filling part chamber 3 that shields the filling part including the filling machine 2 of the drink filling apparatus, a COP (Cleaning Out of Place) process and a SOP (Sterilizing Out of Place) process of the interior of the filling part chamber 3 are performed. Aseptic water is needed to clean the sterilized caps and the outer surfaces of the mouth portions of the containers filled with the drink, so that the drink filling apparatus is provided with an aseptic water producing unit 24. Aseptic water produced by the aseptic water producing unit 24 is stored in an aseptic water tank 25 and supplied to the filling part chamber 3. The aseptic water tank 25 need not be provided, and the produced aseptic water may be circulated in a circulation path formed by the aseptic water producing unit 24 and an aseptic water feedback path 27 described later and directly supplied to the filling part chamber 3 as required. The aseptic water produced by the aseptic water producing unit 24 may be supplied as required to another chamber such as a sterilizing part chamber, a rinsing part chamber or a discharging part chamber or another part of the drink filling apparatus such as a cap sterilizing part, and used to wash the cleaner and a sterilizer away or to cool the part of the drink filling apparatus.

The heating sterilization part 18 includes a first-stage heating portion 12, a second-stage heating portion 13, a holding tube 14, a first-stage cooling portion 15 and a second-stage cooling portion 16, for example. The drink or water supplied from the balance tank 5 is gradually heated while being fed from the first-stage heating portion 12 to the second-stage heating portion 13, heated to a target temperature in the holding tube 14, and then gradually cooled while being fed through the first-stage cooling portion 15 and the second-stage cooling portion 16. The number of stages of the heating portions or cooling portions can be increased or decreased as required. A homogenizer may be disposed before or after the holding tube 14.

The aseptic water producing unit 24 has a similar configuration to the heating sterilization part 18, and includes a first-stage heating portion, a second-stage heating portion, a holding tube, a first-stage cooling portion, and a second-stage cooling portion, for example. The aseptic water producing unit 24 gradually heats supplied water while feeding the water from the first-stage heating portion to the second-stage heating portion, heats the water to a target temperature in the holding tube, and then gradually cools the water while feeding the water through the first-stage cooling portion and the second-stage cooling portion. The number of stages of the heating portions or cooling portions can be increased or decreased as required. The produced aseptic water is temporarily stored in the aseptic water tank 25, and supplies to the filling part chamber 3 as required.

The balance tank 5, the manifold valve 8, the aseptic surge tank 19, the filling machine tank 11, the carbonating unit 21, the carbonated drink surge tank 22, the carbonated drink manifold valve 23 and the aseptic water tank 25 are well-known devices and therefore will not be described in detail herein.

Figure 2:
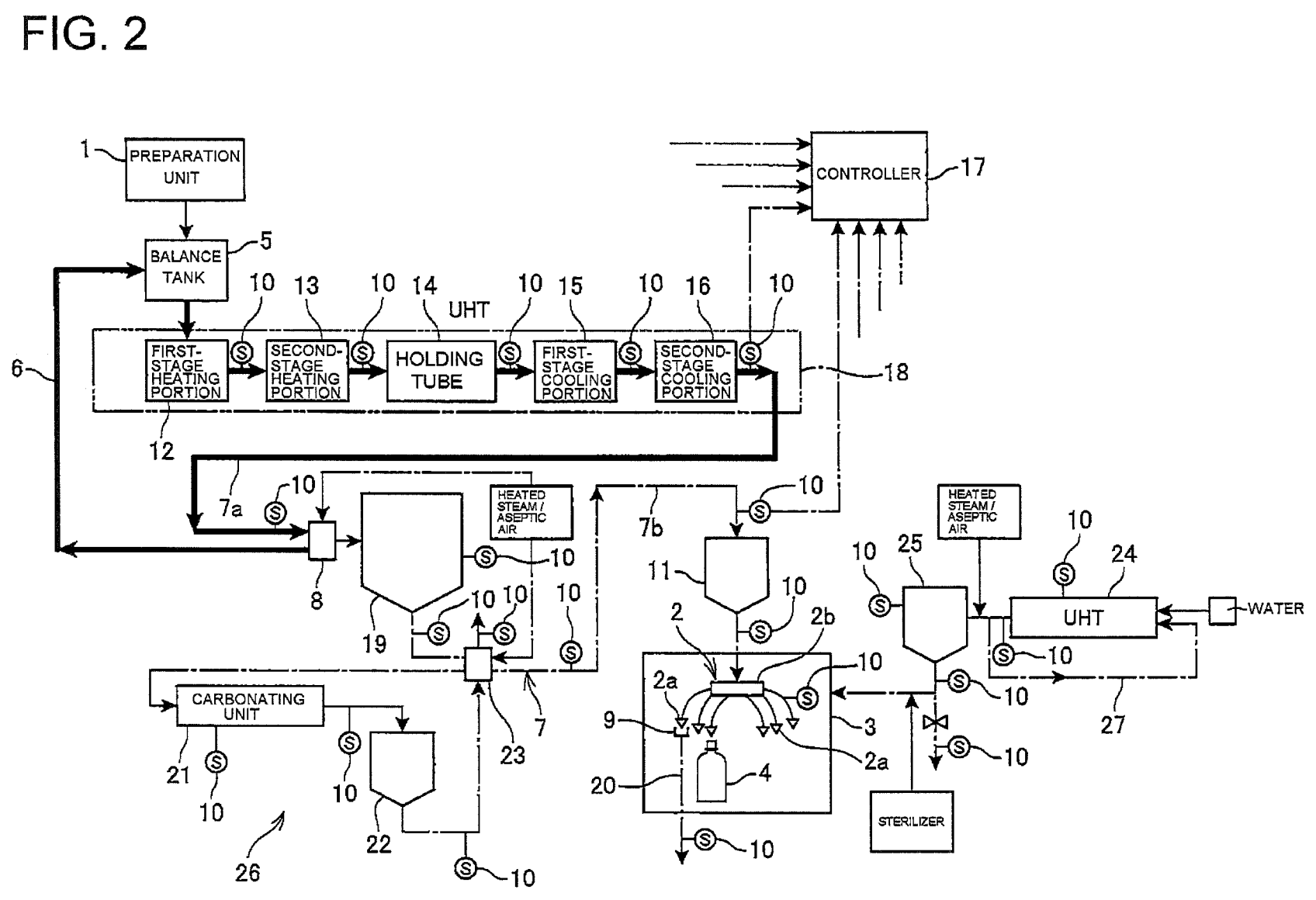

As shown by the bold line in FIG. 2, an upstream-side piping section 7a of the drink supply piping 7, which extends from the balance tank 5 to the manifold valve 8 via the heating sterilization part 18, is provided with an upstream-side feedback path 6 to form a circulation path for performing SIP.

SIP of the upstream-side piping section 7a is performed by passing a heated liquid or heated steam through the upstream-side piping section 7a. Temperature sensors 10 are disposed at positions where the temperature is less likely to increase during SIP. The positions where the temperature is less likely to increase include positions along the pipe line from the first-stage heating portion 12 in the heating sterilization part 18 to the manifold valve 8 such as positions between the portions in the heating sterilization part 18, a position at the outlet of the second-stage cooling portion 16 and a position at the inlet of the manifold valve 8. The temperature sensors 10 are disposed at these positions. Temperature information measured by the temperature sensors 10 is transmitted to a controller 17.

The "heated liquid" refers to heated water or a heated cleaning liquid. The "water" can refer to any water that contains no foreign matters, such as ion-exchanged water, distilled water or tap water. The "cleaning liquid" refers to a liquid containing water and an acidic compound or a basic compound. Here, the "water" is the water described above. The "acidic compound" refers to an inorganic acid such as hydrogen peroxide, hydrochloric acid, nitric acid or phosphoric acid, or an organic acid such as peracetic acid, acetic acid, formic acid, octanoic acid, oxalic acid, citric acid, succinic acid or gluconic acid. The "basic compound" refers to an inorganic basic compound such as sodium hydroxide or potassium hydroxide, or an organic basic compound such as ethanolamine or diethylamine. The "cleaning liquid" may further include a metal-ion blocking agent such as an alkali metal salt, an alkaline earth metal salt or an ammonium salt of an organic acid or an ethylenediamine tetraacetic acid, an anionic surfactant, a cationic surfactant, a nonionic surfactant such as a polyoxyethylene alkylphenyl ether, a solubilizer such as sodium cumenesulfonate, an acid-based polymer such as polyacrylic acid or a metal salt thereof, a corrosion inhibitor, a preservative, an antioxidant, a dispersant or a defoaming agent, for example.

The "heating" refers to heating water or a cleaning liquid to a temperature suitable for SIP, and the acidic compound or basic compound contained in the cleaning liquid is expected to improve the sterilization effect compared with water heated to the same temperature. The temperature suitable for SIP is typically 121.1° C. or higher. However, depending on the drink used for filling by the drink filling apparatus, the temperature need not be 121.1° C. or higher. For example, for a highly acidic drink with a pH less than 4.0, the temperature can be 65° C. or higher. In some cases, furthermore, when the pH of the drink is equal to or higher than 4.0 and lower than 4.6, the temperature can be 85° C. or higher.

The "heated steam" refers to steam produced by heating water containing no foreign matters such as ion-exchanged water, distilled water or tap water. Although the heated steam typically has a temperature of 121.1° C. or higher, the temperature can be 100° C. or higher in some cases. The steam is produced by directly heating water. Alternatively, however, the steam may be produced by indirectly heating water using steam produced by a boiler as a heat source.

Figure 3:
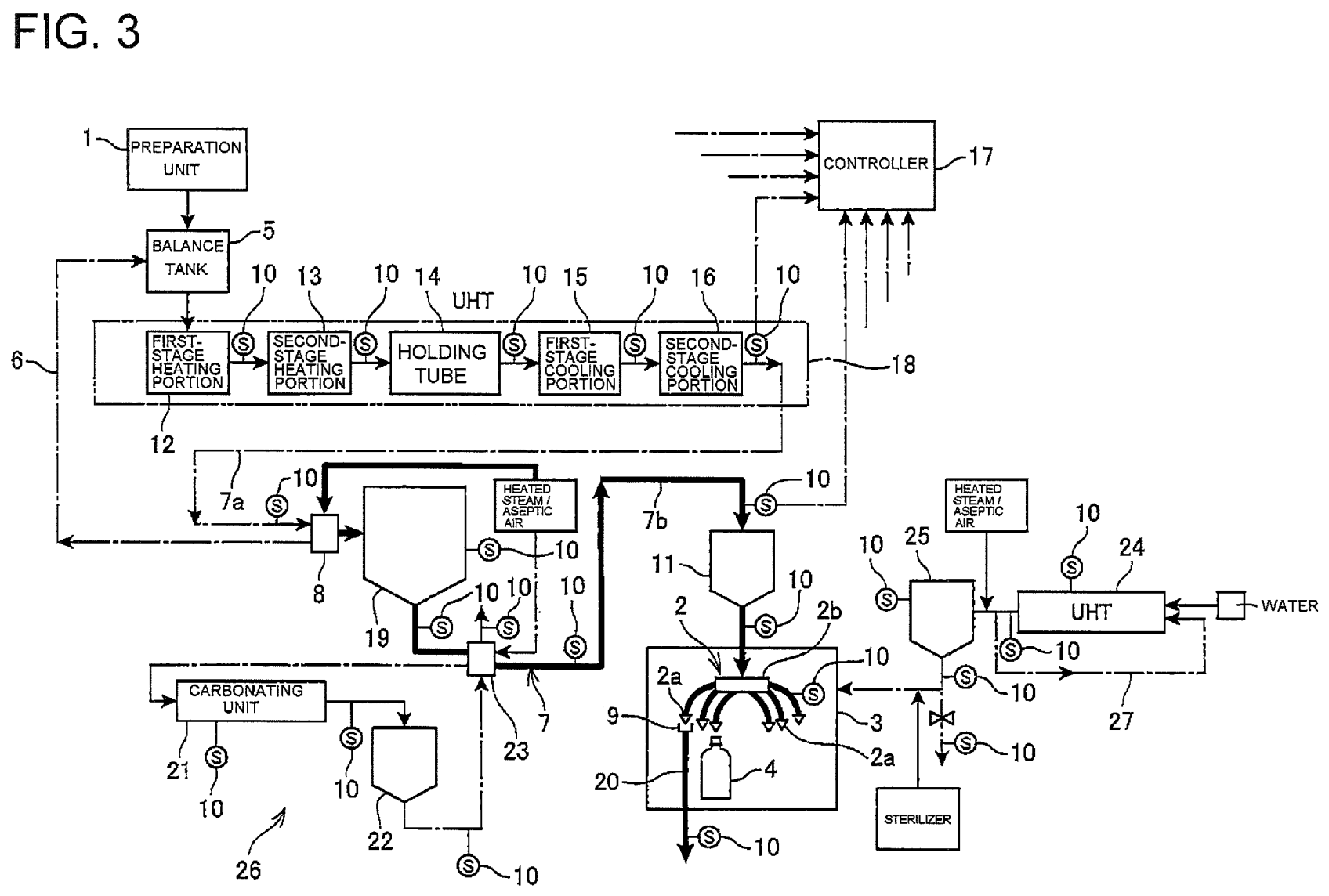

As shown by the bold line in FIG. 3, a downstream-side piping section 7b of the drink supply piping 7, which extends from the manifold valve 8 located downstream of the upstream-side piping section 7a to the filling machine 2 via the aseptic surge tank 19 and the filling machine tank 11, is also provided with temperature sensors 10 at positions where the temperature is less likely to increase when the heated liquid or heated steam is passed through the interior thereof. For example, the positions where the temperature is less likely to increase include positions along the pipe line from the aseptic surge tank 19 to the filling nozzles 2a, such as a position in the vicinity of the outlet of the aseptic surge tank 19, a midway bent point, positions in the vicinities of the inlet and outlet of the filling machine tank 11, positions between a manifold 2b and the filling nozzles 2a in the filling machine 2, and the filling nozzles 2a. The temperature sensors 10 are disposed at these positions along the pipe line. Temperature information measured by the temperature sensors 10 is transmitted to the controller 17 provided in the drink filling apparatus. All the filling nozzles 2a are preferably provided with a temperature sensor 10.

As shown in FIG. 1, when the drink filling apparatus performs filling with a carbonated drink, the downstream-side piping section 7b is provided with the carbonating unit 21 and the carbonated drink surge tank 22 for storing the carbonated drink between the aseptic surge tank 19 for storing the sterilized drink and the filling machine tank 11 for storing the drink immediately before filling. To supply the carbonated drink, the carbonated drink manifold valve 23 is provided between the aseptic surge tank 19 and the filling machine tank 11. The path extending from the carbonated drink manifold valve 23 back to the carbonated drink manifold valve 23 via the carbonating unit 21 and the carbonated drink surge tank 22 is a carbonating piping section 26, and the carbonating piping section 26 includes the carbonated drink manifold valve 23, the carbonating unit 21 and the carbonated drink surge tank 22.

Figure 5:
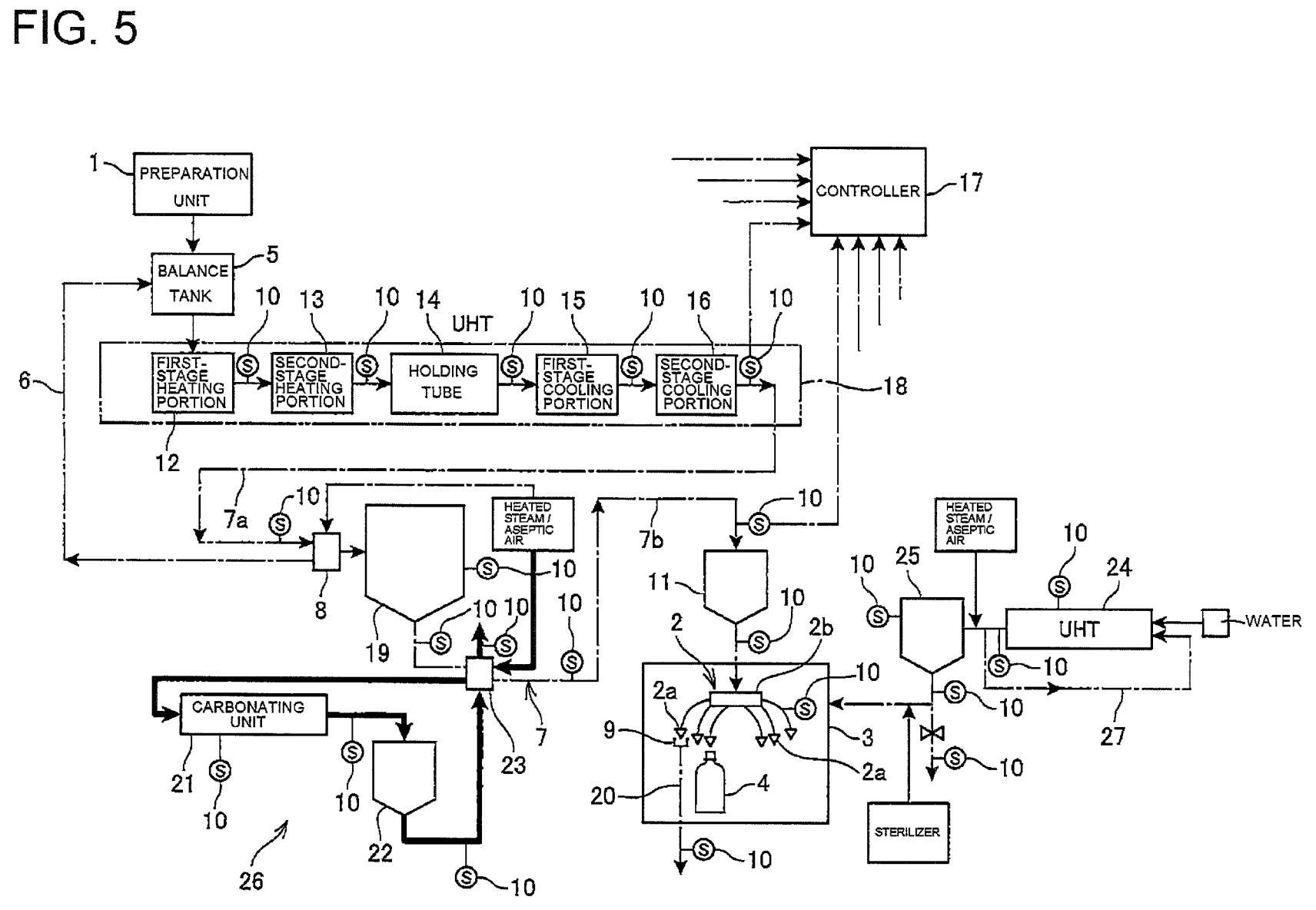

As shown by the bold line in FIG. 5, temperature sensors 10 are disposed at positions where the temperature is less likely to increase when the heated liquid or heated steam is passed through the carbonating piping section 26. For example, the positions where the temperature is less likely to increase include a position in the carbonating unit 21, a position in the vicinity of the outlet of the carbonating unit 21, and positions along the pipe line from the carbonated drink surge tank 22 to the carbonated drink manifold valve 23, such as a position in the vicinity of the outlet of the carbonated drink surge tank 22 and a midway bent point, and the temperature sensors 10 are disposed at these positions along the pipe line. Temperature information measured by the temperature sensors 10 is transmitted to the controller 17 provided in the drink filling apparatus.

Figure 7:
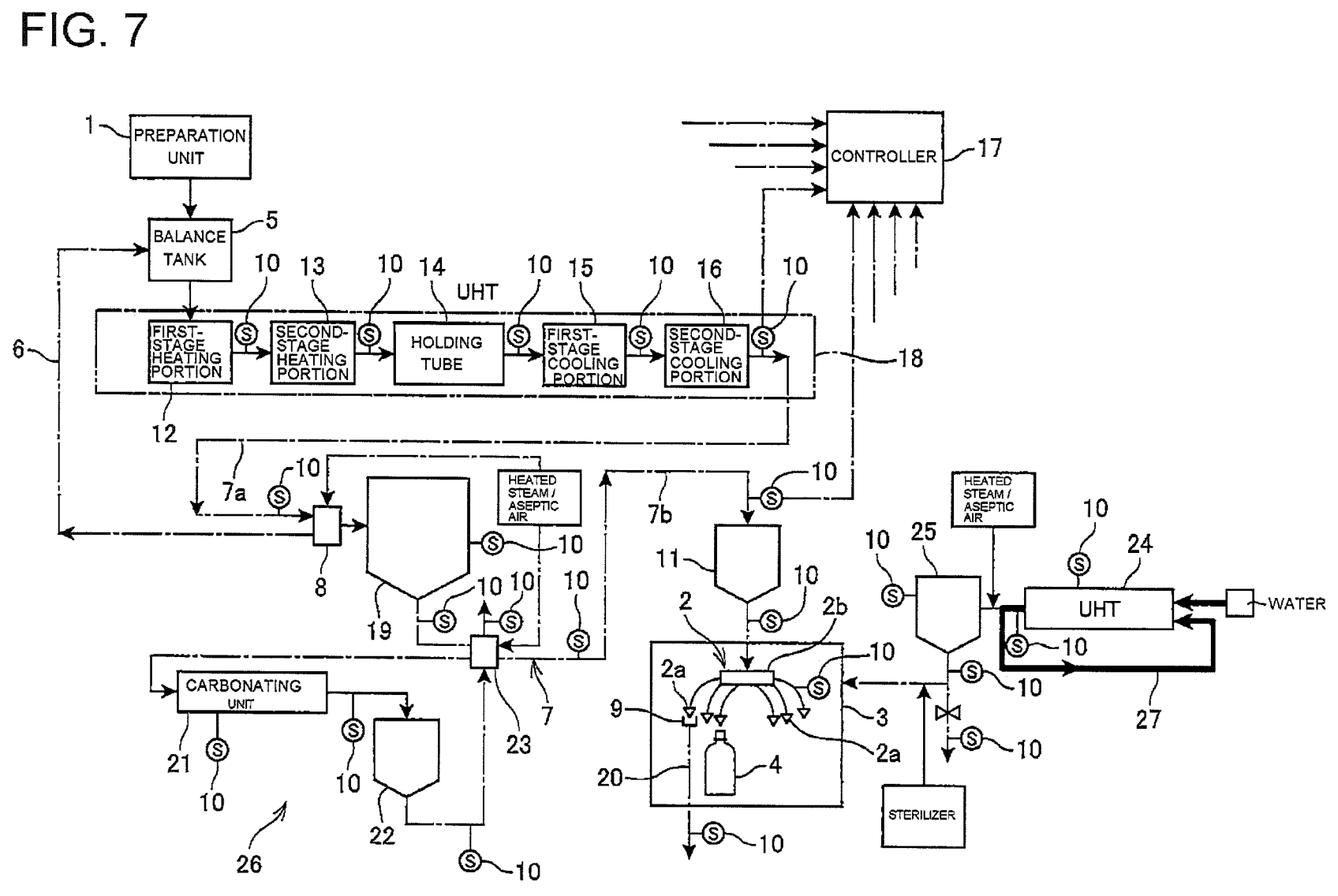

As shown by the bold line in FIG. 7, the aseptic water producing unit 24 provided in the drink filling apparatus is provided with an aseptic water feedback path 27 to form an aseptic water circulation path for performing SIP of the aseptic water producing unit 24.

SIP of the aseptic water producing unit 24 and the aseptic water feedback path 27 is performed by passing a heated liquid or heated steam therethrough. Temperature sensors 10 are disposed at positions where the temperature is less likely to increase during SIP. For example, the positions where the temperature is less likely to increase include positions along the pipe line from the first-stage heating portion in the aseptic water producing unit 24 to the outside of the aseptic water producing unit 24, such as positions between the portions in the aseptic water producing unit 24 and a position at the outlet of the second-stage cooling portion, and the temperature sensors 10 are disposed at these positions. Temperature information measured by the temperature sensors 10 is transmitted to the controller 17.

The aseptic water produced by the aseptic water producing unit 24 is stored in the aseptic water tank 25. SIP of the aseptic water tank 25 is performed by passing a heated liquid or heated steam through the aseptic water tank 25. The temperature sensors 10 are disposed at positions where the temperature is less likely to increase when the heated liquid or heated steam is passed through the aseptic water tank 25. For example, the positions include the aseptic water tank 25, a position in the vicinity of the outlet of the aseptic water tank 25, and a midway bent point.

In the downstream-side piping section 7b, a cup 9 is provided for an opening of each filling nozzle 2a in the filling machine 2 for SIP, and the cup 9 can be brought closer to and separated from the filling nozzle 2a. To perform SIP, an actuator (not shown) puts each cup 9 on the opening at the tip end of the filling nozzle 2a in the filling machine 2 to connect a leading end of a drain tube 20 to the opening of the filling nozzle 2a.

The manifold valve 8, the carbonated drink manifold valve 23 and the actuator (not shown) provided on the drink supply piping 7 of the drink filling apparatus, as well as various switching valves, pumps and the like are controlled by the controller 17.

Next, a sterilization method for the drink filling apparatus described above will be described with reference to FIGS. 2 to 9.

When an operation button on a panel (not shown) of the controller 17 is manipulated, SIP is performed for each of the upstream-side piping section 7a and the downstream-side piping section 7b of the drink supply piping 7 in a predetermined procedure (see FIGS. 2 and 3). Before SIP is started, the manifold valve 8 disconnects the upstream-side piping section 7a and the downstream-side piping section 7b from each other.

SIP of the upstream-side piping section 7a and SIP of the downstream-side piping section 7b can be performed sequentially or in parallel. It is also possible that the upstream-side piping section 7a and the downstream-side piping section 7b are not separated from each other, and SIP of the whole of the drink supply piping is performed at the same time by passing the heated liquid or heated steam from the upstream side to the downstream side and circulating the heated liquid or heated steam with the filling nozzles 2a covered with the cups 9. The heated liquid or heated steam need not be circulated, and SIP may be performed by discharging the heated liquid or heated steam having passed through the filling nozzles 2a.

Water or a cleaning liquid is fed from a water supply source (not shown) into the circulation path via the balance tank 5, the fed water or cleaning liquid is heated in the heating sterilization part 18, and the heated water or cleaning liquid sterilizes the flow path while circulating in the circulation path. In this way, SIP of the interior of the upstream-side piping section 7a is performed.

While the heated liquid is flowing in the upstream-side piping section 7a, a plurality of temperatures detected at predetermined time intervals by the temperature sensors 10 disposed at different positions along the upstream-side piping section 7a is transmitted from the temperature sensors 10 to the controller 17 at regular time intervals. The controller 17 selects the lowest temperature from the temperatures detected at predetermined time intervals, and calculates an F value from the temperature. Since the controller 17 selects the lowest temperature, the temperature sensor 10 that detects the selected temperature may vary. This is because, although the temperature sensors 10 detect temperature at predetermined time intervals and transmit the temperatures to the controller 17, the lowest one of the detected temperatures is not always the temperature at the same position.

SIP of the upstream-side piping section 7a may be performed by passing heated steam through the upstream-side piping section 7a from the inlet of the heating sterilization part 18 and discharging the heated steam from the manifold valve 8.

Figure 10:
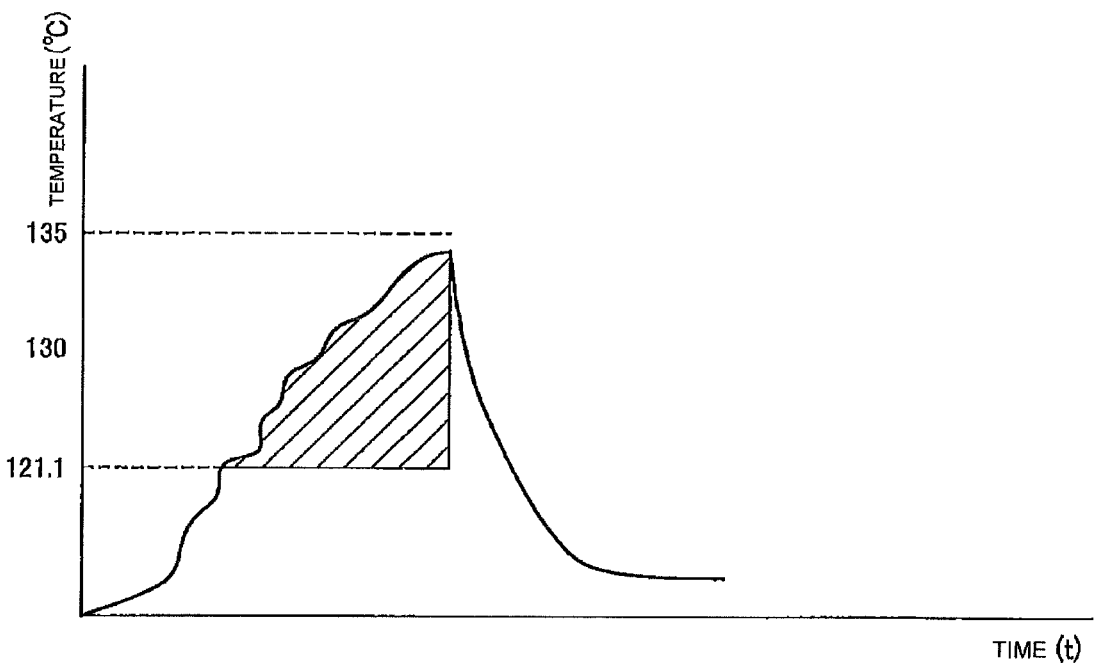
FIG. 10 is a graph showing a relationship between temperature and time of a method of heating the drink supply piping.

As shown in FIG. 10, of the temperatures at different positions raised by heating by the hot water or heated cleaning liquid, when the selected lowest temperature reaches 121.1° C., the controller 17 starts calculating the F value from the lowest temperature according to the following formula.

$$F = \int_{t_0}^{t_1} 10^{(T-121.1)/10} dt \qquad \text{[Formula 2]}$$

Where T denotes an arbitrary sterilization temperature (° C.), $10^{(T-121.1)/10}$ represents a fatality rate at an arbitrary temperature T and corresponds to a heating duration (in minutes) at 121.1° C., which is a reference temperature, and 10 denotes a Z value (° C.).

For a highly acidic drink with a pH less than 4.0, the reference temperature may be 65° C., rather than 121.1° C. For a drink with a pH equal to or higher than 4.0 and lower than 4.6, the reference temperature may be 85° C. or higher. If the lowest temperature becomes lower than the reference temperature during integration of the F value, although the integration of the F value can be suspended and resumed after the lowest temperature becomes higher than the reference temperature again, it is preferable to stop SIP, reset the integration of the F value, and restart SIP.

Figure 11:
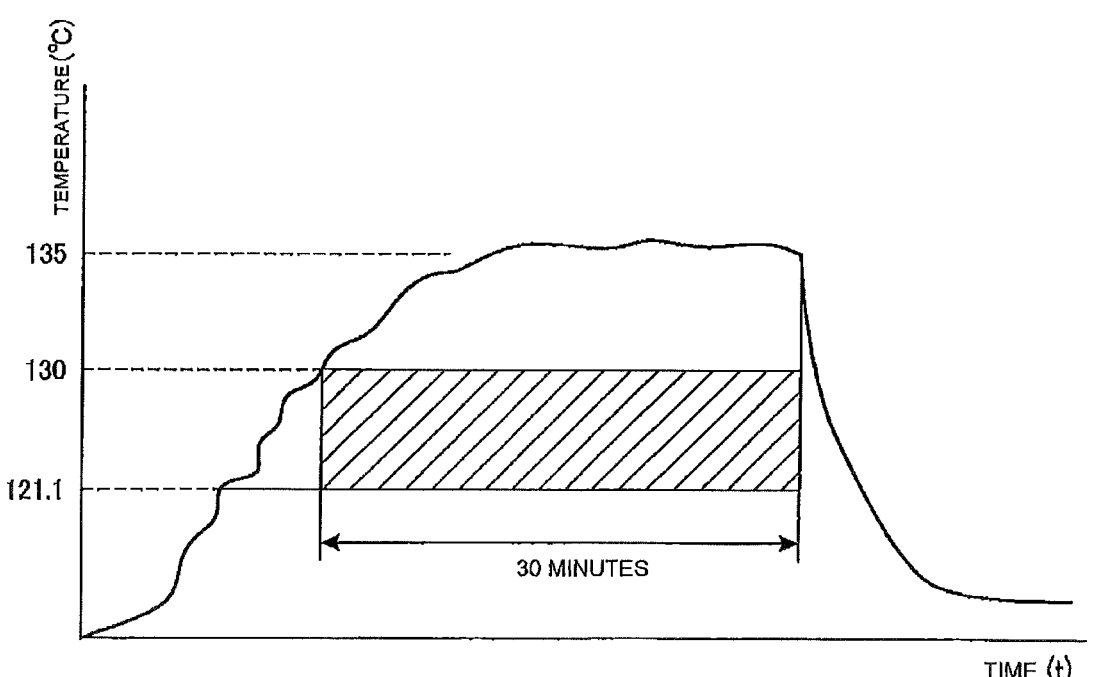
FIG. 11 is a graph showing a relationship between temperature and time of a conventional method of heating the drink supply piping.

The controller 17 integrates the F value for the lowest temperature calculated according to the formula described above, and when the integrated F value reaches a target value, the controller 17 instructs to end the sterilization step, which is SIP, of the upstream-side piping section 7a. In response to the instruction, cooling water is supplied to the first-stage cooling portion 15 and the second-stage cooling portion 16, and the water or cleaning liquid is cooled and kept continuously circulating while waiting for the start of sterilization of the drink. When a cleaning liquid is used for performing SIP, the cleaning liquid is washed away by aseptic water, and then the aseptic water is kept continuously circulating while waiting. The target value of the F value corresponds to the area of the hatched part in FIG. 10. The target value also corresponds to the area of the hatched part in FIG. 11. As is obvious from the comparison between FIGS. 10 and 11, the heating duration, which is conventionally 30 minutes, is substantially reduced.

After that, the drink is fed from the preparation unit 1 to the balance tank 5 to start sterilization of the drink. When the water is replaced with the drink, the upstream-side piping section 7a and the upstream-side feedback path 6 are disconnected from each other, and the sterilized drink is stored in the aseptic surge tank 19.

At the same time as, or in advance of, the start of SIP of the upstream-side piping section 7a, SIP of the downstream-side piping section 7b including the aseptic surge tank 19 is started.

After the cups 9 are put on the openings of the filling nozzles 2a, and the drain tube 20 is connected to the filling nozzles 2a, heated steam is supplied from a heated steam supply source into the aseptic surge tank 19 and the filling machine tank 11 as shown by the bold line in FIG. 3. The heated steam is fed to the aseptic surge tank 19 via the manifold valve 8 and flows through the carbonated drink manifold valve 23 to the filling machine tank 11 and then to the filling nozzles 2a in the downstream-side piping section 7b to heat these components. After that, the heated steam is collected into a single pipe from all the cups 9 and discharged to the outside of the filling machine 2 through the drain tube 20.

While the heated steam is flowing in the downstream-side piping section 7b, a plurality of temperatures detected at predetermined time intervals by the temperature sensors 10 disposed at different positions along the downstream-side piping section 7b is transmitted from the temperature sensors 10 to the controller 17 at regular time intervals. The plurality of temperatures detected by the temperature sensors 10 is transmitted to the controller 17, and the controller 17 selects the lowest temperature from the received temperatures, and calculates the F value from the temperature. Since the controller 17 selects the lowest temperature, the temperature sensor 10 that detects the selected temperature may vary. This is because, although the temperature sensors 10 detect temperature at predetermined time intervals and transmit the temperatures to the controller 17, the lowest one of the detected temperatures is not always the temperature at the same position.

As shown in FIG. 10, of the temperatures at different positions raised by heating by the heated steam, when the selected lowest temperature reaches 121.1° C., the controller 17 starts calculating the F value from the lowest temperature.

The controller 17 integrates the calculated F value, and when the integrated F value reaches a target value, the controller 17 instructs to end the sterilization step, which is SIP, of the downstream-side piping section 7b. The supply of the heated steam from the aseptic surge tank 19 to the filling nozzles through the downstream-side piping section 7b is stopped. The target value of the F value corresponds to the area of the hatched part in FIG. 10 described above. As is obvious from the comparison between FIGS. 10 and 11, the SIP duration for the interior of the downstream-side piping section 7b is also substantially reduced compared with the conventional SIP duration.

A pipe line may be provided from the cups 9 to the manifold valve 8, a heating unit may be provided on the pipe line, and SIP of the downstream-side piping section 7b may be performed by passing water or a cleaning liquid into the downstream-side piping section 7b through the manifold valve 8, circulating the water or cleaning liquid in a downstream-side circulation path, which is formed by providing the pipe line, and heating the water or cleaning liquid used as the heated liquid with the heating unit. When the cleaning liquid is used as the heated liquid, the cleaning liquid is washed away by aseptic water.

After SIP of the downstream-side piping section 7b ends, aseptic air is fed into the downstream-side piping section 7b through the manifold valve 8 in the same manner as the heated steam to cool the interior of the downstream-side piping section 7b to room temperature, for example. The drain tube 20 is then disconnected. Furthermore, an actuator (not shown) removes the cups 9 from the openings of the filling nozzles 2a.

After SIP of the aseptic surge tank 19 and the following downstream-side piping section 7b ends, the drink flows from the heating sterilization part 18 to the aseptic surge tank 19 through the upstream-side piping section 7a and is stored in the aseptic surge tank 19. The drink then flows through the downstream-side piping section 7b, and the operation of filling the bottles 4 with the drink is started.

Figure 8:
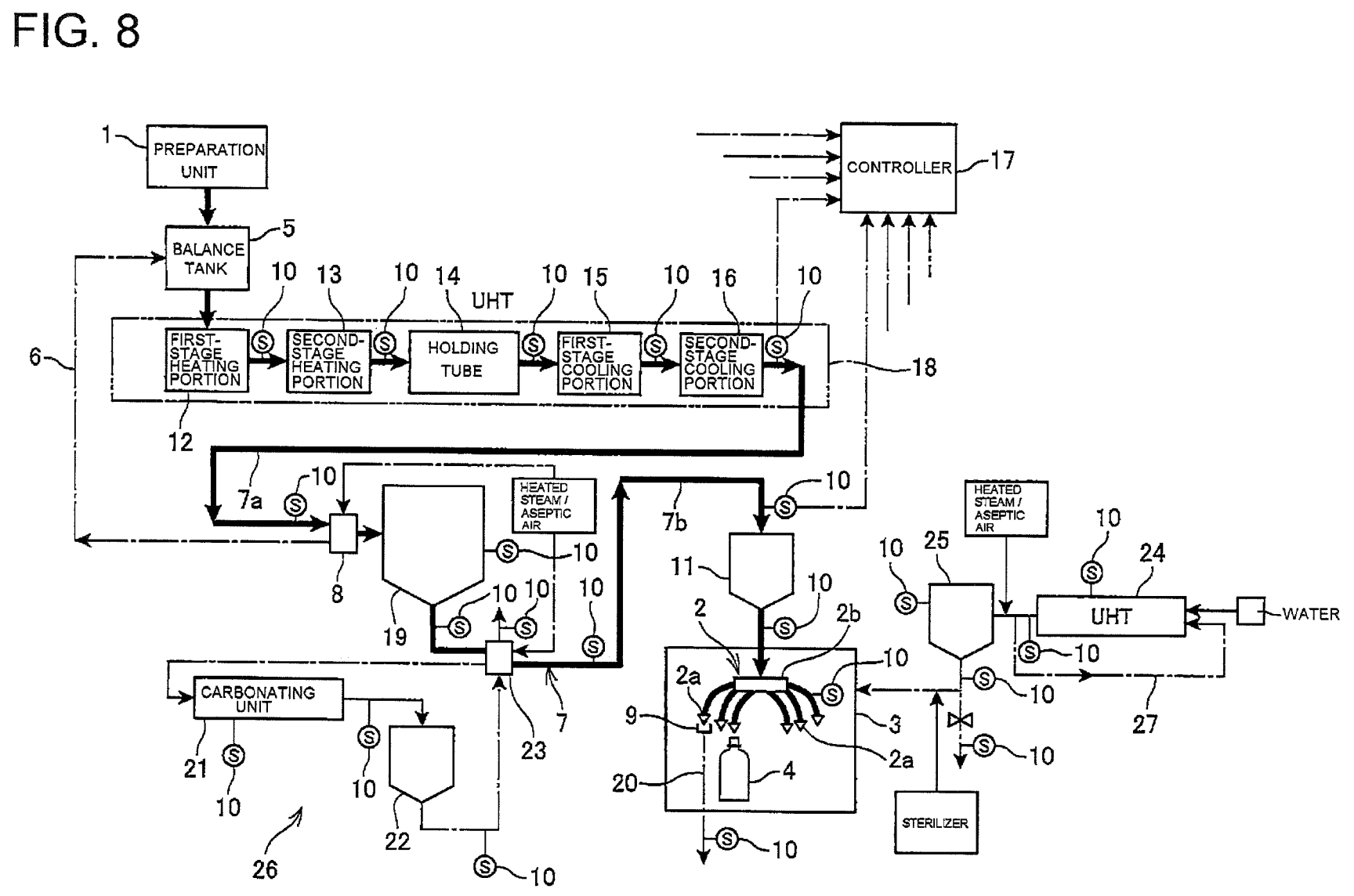

As shown by the bold line in FIG. 8, the drink prepared in the preparation unit 1 flows to the interior of the filling machine 2 through the sterilized upstream-side piping section 7a and downstream-side piping section 7b of the drink supply piping 7, and the bottles 4, which are containers, are filled with the drink from the filling nozzles 2a of the filling machine 2. The bottles 4 filled with the drink are capped by a capper (not shown) and then fed to the outside of the filling machine 2.

SIP of the part from the aseptic surge tank 19 to the filling nozzles 2a can be performed by supplying heated steam to the downstream-side piping section 7b as described above. In that case, however, the flow path is long, the temperature of the heated steam can decrease while the heated steam flows to the filling nozzles 2a, and therefore, it may take a long time to raise the temperature of the filling nozzles 2a to 121.1° C. To avoid this, the heated steam may be supplied to the manifold valve 8 and the carbonated drink manifold valve 23 so that SIP of the aseptic surge tank 19 and SIP of the filling piping section from the filling machine tank 11 to the filling nozzles 2a are separately performed, and the ends of the sterilizations may be separately determined.

Figure 4:
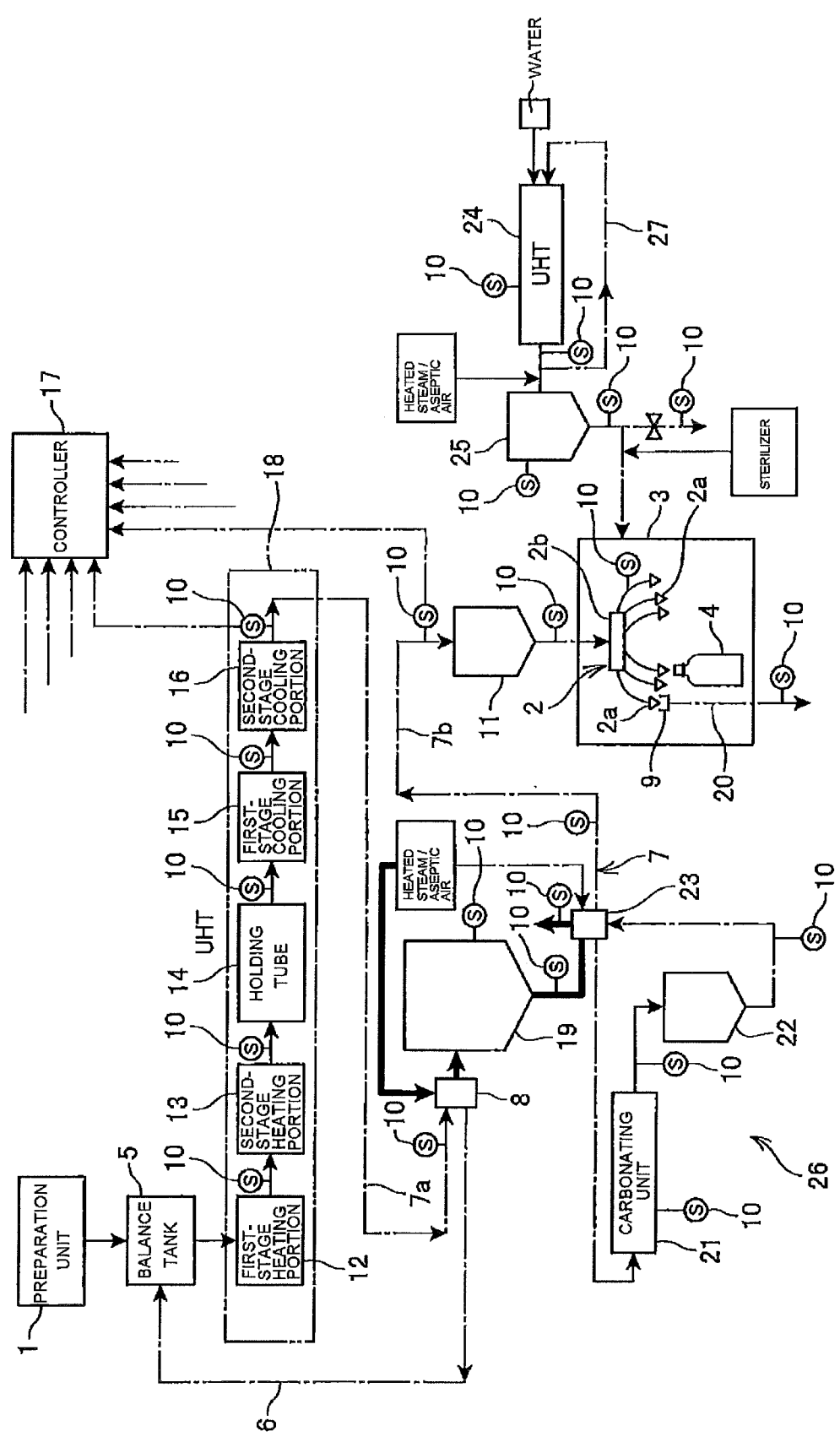
FIG. 4 is a block diagram showing the drink supply piping in the drink filling apparatus according to the embodiment of the present invention, in which the aseptic surge tank is being subjected to SIP.

As shown by the bold line in FIG. 4, the heated steam is supplied from the heated steam supply source to the interior of the aseptic surge tank 19. The heated steam is fed to the aseptic surge tank 19 through the manifold valve 8, and discharged through the carbonated drink manifold valve 23.

While the heated steam is flowing from the manifold valve 8 through the aseptic surge tank 19, a plurality of temperatures detected at predetermined time intervals by the temperature sensors 10 disposed at different positions is transmitted from the temperature sensors 10 to the controller 17 at regular time intervals. The plurality of temperatures detected by the temperature sensors 10 is transmitted to the controller 17, and the controller 17 selects the lowest temperature from the received temperatures, and calculates the F value from the temperature. Since the controller 17 selects the lowest temperature, the temperature sensor 10 that detects the selected temperature may vary. This is because, although the temperature sensors 10 detect temperature at predetermined time intervals and transmit the temperatures to the controller 17, the lowest one of the detected temperatures is not always the temperature at the same position.

Of the temperatures at different positions raised by heating by the heated steam, when the lowest temperature reaches 121.1° C., the controller 17 starts calculating the F value from the lowest temperature. The controller 17 integrates the calculated F value, and when the integrated F value reaches a target value, the controller 17 instructs to end the sterilization step, which is SIP, of the part from the manifold valve 8 to the carbonated drink manifold valve 23 via the aseptic surge tank 19. The supply of the heated steam to the aseptic surge tank 19 is stopped, aseptic air is supplied to the manifold valve 8, the aseptic surge tank 19 and the carbonated drink manifold valve 23, the aseptic surge tank 19 is cooled and kept aseptic while waiting for the operation of the drink filling apparatus.

Figure 6:
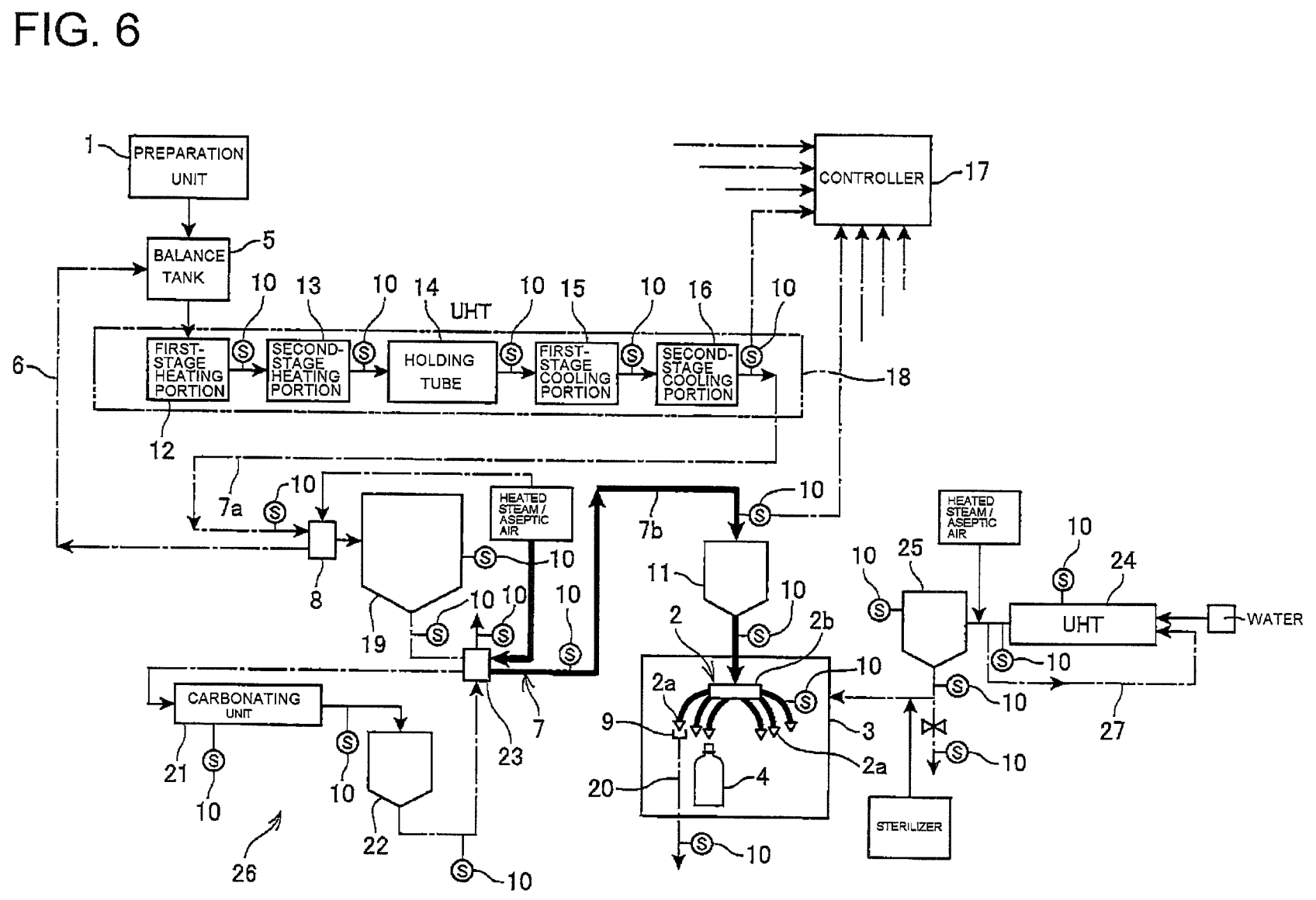

As shown by the bold line in FIG. 6, the heated steam is supplied from the heated steam supply source to the filling piping section from the filling machine tank 11 to the filling nozzles 2a. The heated steam is fed to the filling nozzles 2a through the carbonated drink manifold valve 23 and the filling machine tank 11 to heat these components. After that, the heated steam is collected into a single pipe from all the cups 9 and discharged to the outside of the filling machine 2 through the drain tube 20.

While the heated steam is flowing in the filling piping section from the carbonated drink manifold valve 23 to the filling nozzles 2a via the filling machine tank 11, a plurality of temperatures detected at predetermined time intervals by the temperature sensors 10 disposed at different positions is transmitted from the temperature sensors 10 to the controller 17 at regular time intervals. The plurality of temperatures detected by the temperature sensors 10 is transmitted to the controller 17, and the controller 17 selects the lowest temperature from the received temperatures, and calculates the F value from the temperature. Since the controller 17 selects the lowest temperature, the temperature sensor 10 that detects the selected temperature may vary. This is because, although the temperature sensors 10 detect temperature at predetermined time intervals and transmit the temperatures to the controller 17, the lowest one of the detected temperatures is not always the temperature at the same position.

Of the temperatures at different positions raised by heating by the heated steam, when the lowest temperature reaches 121.1° C., the controller 17 starts calculating the F value according to the lowest temperature. The controller 17 integrates the calculated F value, and when the integrated F value reaches a target value, the controller 17 instructs to end the sterilization step, which is SIP, of the filling piping section from the carbonated drink manifold valve 23 to the filling nozzles 2a via the filling machine tank 11. The supply of the heated steam to the carbonated drink manifold valve 23 is stopped, aseptic air is supplied to the part from the carbonated drink manifold valve 23 to the filling nozzles 2a via the filling machine tank 11, the flow path from the carbonated drink manifold valve 23 to the filling nozzles 2a via the filling machine tank 11 is cooled and kept aseptic while waiting for the operation of the drink filling apparatus.

SIP of the filling piping section from the carbonated drink manifold valve 23 to the filling nozzles 2a via the filling machine tank 11 may be performed by supplying a heated liquid, rather than the heated steam, to the carbonated drink manifold valve 23. When a cleaning liquid is used as the heated liquid, the flow path from the carbonated drink manifold valve 23 to the filling nozzles 2a via the filling machine tank 11 is washed with aseptic water.

When a carbonated drink is produced by carbonating a drink, the drink filling apparatus includes the carbonating unit 21 and the carbonated drink surge tank 22 between the aseptic surge tank 19 and the filling machine tank 11, and includes the carbonated drink manifold valve 23 to flow the carbonated drink to the drink supply piping 7. When the drink filling apparatus fills the bottles 4 with a carbonated drink that needs to be sterilized, the carbonating piping section 26 extending from the carbonated drink manifold valve 23 back to the carbonated drink manifold valve 23 via the carbonating unit 21 and the carbonated drink surge tank 22 also has to be subjected to SIP before operation of the drink filling apparatus.

For SIP of the carbonating piping section 26, as shown by the bold line in FIG. 5, the heated steam is supplied from the heated steam supply source to the flow path extending from the carbonated drink manifold valve 23 back to the carbonated drink manifold valve 23 via the carbonating unit 21 and the carbonated drink surge tank 22. The heated steam is fed to the carbonated drink manifold valve 23 and flows back to the carbonated drink manifold valve 23 through the carbonating unit 21 and the carbonated drink surge tank 22. The heated steam heats these components and then is discharged through the carbonated drink manifold valve 23.

While the heated steam is flowing from the carbonated drink manifold valve 23 back to the carbonated drink manifold valve 23 via the carbonating unit 21 and the carbonated drink surge tank 22, a plurality of temperatures detected at predetermined time intervals by the temperature sensors 10 disposed at different positions is transmitted from the temperature sensors 10 to the controller 17 at regular time intervals. The plurality of temperatures detected by the temperature sensors 10 is transmitted to the controller 17, and the controller 17 selects the lowest temperature from the received temperatures, and calculates the F value from the temperature. Since the controller 17 selects the lowest temperature, the temperature sensor 10 that detects the selected temperature may vary. This is because, although the temperature sensors 10 detect temperature at predetermined time intervals and transmit the temperatures to the controller 17, the lowest one of the detected temperatures is not always the temperature at the same position.

Of the temperatures at different positions raised by heating by the heated steam, when the lowest temperature reaches 121.1° C., the controller 17 starts calculating the F value from the lowest temperature. The controller 17 integrates the calculated F value, and when the integrated F value reaches a target value, the controller 17 instructs to end the sterilization step, which is SIP, of the carbonating piping section 26 extending from the carbonated drink manifold valve 23 back to the carbonated drink manifold valve 23 via the carbonating unit 21 and the carbonated drink surge tank 22. The supply of the heated steam to the carbonated drink manifold valve 23 is stopped, aseptic air is supplied to the part extending from the carbonated drink manifold valve 23 back to the carbonated drink manifold valve 23 via the carbonating unit 21 and the carbonated drink surge tank 22, and the carbonating piping section 26 is cooled and kept aseptic while waiting for the operation of the drink filling apparatus.

SIP of the carbonating piping section 26 may be performed by supplying a heated liquid, rather than the heated steam, to the carbonated drink manifold valve 23. When a cleaning liquid is used as the heated liquid, the flow path of the carbonating piping section 26 is washed with aseptic water.

Figure 9:
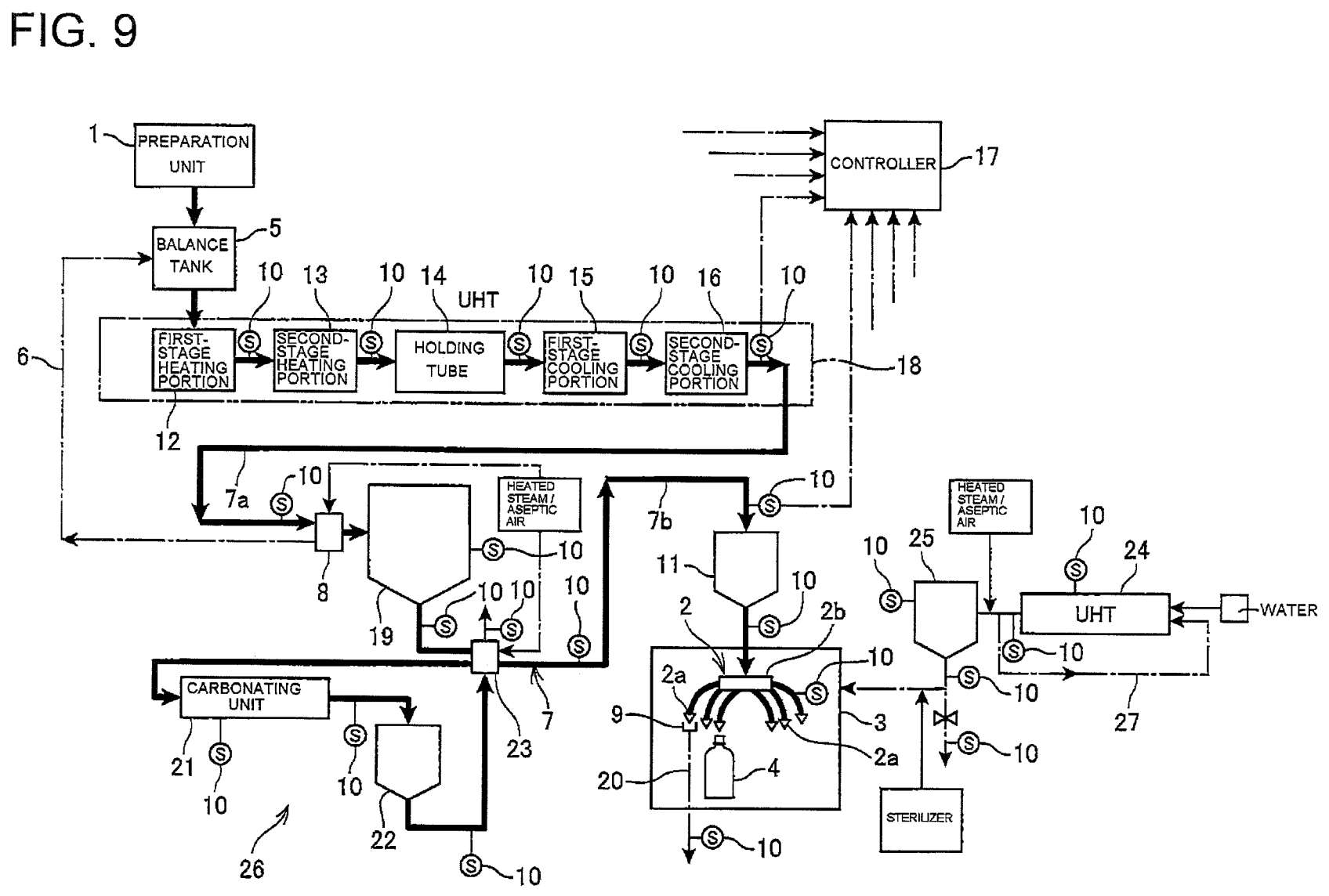

When the drink filling apparatus fills the bottles 4 with a carbonated drink that needs to be sterilized, as shown by the bold line in FIG. 9, the drink prepared in the preparation unit 1 is sterilized, the sterilized drink is stored in the aseptic surge tank 19, then flows from the aseptic surge tank 19 to the carbonating unit 21 via the carbonated drink manifold valve 23, and is carbonated by the carbonating unit 21, the carbonated drink is stored in the carbonated drink surge tank 22 and then flows to the interior of the filling machine 2 through the carbonated drink manifold valve 23 and the filling machine tank 11, and the bottles 4, which are containers, are filled with the carbonated drink through the filling nozzles 2a of the filling machine 2. The bottles 4 filled with the carbonated drink are capped by the capper (not shown) and then fed to the outside of the filling machine 2.

With the drink filling apparatus including the aseptic water producing unit 24 that supplies aseptic water into the filling part chamber that shields the filling part, as shown by the bold line in FIG. 7, an aseptic water supply piping section passing through the aseptic water producing unit 24 is provided with the aseptic water feedback path 27 to form an aseptic water circulation path, and SIP of the aseptic water producing unit 24 is performed by passing a heated liquid through the aseptic water circulation path. Water is fed from the water supply source into the aseptic water circulation path, and the water is heated and sterilized by the aseptic water producing unit 24 while circulating in the aseptic water circulation path, thereby performing SIP of the interior of the aseptic water producing unit 24.

While the heated liquid is flowing in the aseptic water producing unit 24, a plurality of temperatures detected at predetermined time intervals by the temperature sensors 10 disposed at different positions in the aseptic water producing unit 24 is transmitted from the temperature sensors 10 to the controller 17 at regular time intervals. The controller 17 selects the lowest temperature from the temperatures detected at predetermined time intervals, and calculates the F value from the temperature. Since the controller 17 selects the lowest temperature, the temperature sensor 10 that detects the selected temperature may vary. This is because, although the temperature sensors 10 detect temperature at predetermined time intervals and transmit the temperatures to the controller 17, the lowest one of the detected temperatures is not always the temperature at the same position.

Temperatures at a plurality of positions in the aseptic water producing unit 24 are detected at predetermined time intervals, the lowest temperature is selected from the detected temperatures, the F value is calculated for the selected lowest temperature, the calculated F value is integrated, and when the integrated F value reaches a target value, the controller 17 instructs to end the sterilization step, which is SIP, of the aseptic water producing unit 24.

In response to the instruction, cooling water is supplied to the first-stage cooling portion and the second-stage cooling portion, and the heated liquid is cooled and kept continuously circulating while waiting for use of aseptic water. When a cleaning liquid is used as the heated liquid, the aseptic water circulation path is washed with aseptic water.

SIP of the aseptic water producing unit 24 may be performed by passing a heated steam to the inlet of the aseptic water producing unit 24 and discharging the heated steam from the outlet of the aseptic water producing unit 24.

The aseptic water produced by the aseptic water producing unit 24 is stored in the aseptic water tank 25. SIP is performed by passing the heated steam to the aseptic water tank 25 and discharging the heated steam downstream of the aseptic water tank 25. A plurality of temperatures detected at predetermined time intervals by the temperature sensors 10 disposed at different positions in the aseptic water tank 25 is transmitted from the temperature sensors 10 to the controller 17 at regular time intervals. The controller 17 selects the lowest temperature from the temperatures detected at predetermined time intervals, and calculates the F value from the temperature. Since the controller 17 selects the lowest temperature, the temperature sensor 10 that detects the selected temperature may vary. This is because, although the temperature sensors 10 detect temperature at predetermined time intervals and transmit the temperatures to the controller 17, the lowest one of the detected temperatures is not always the temperature at the same position.

Temperatures at a plurality of positions in the aseptic water tank 25 are detected at predetermined time intervals, the lowest temperature is selected from the detected temperatures, the F value is calculated for the selected lowest temperature, the calculated F value is integrated, and when the integrated F value reaches a target value, the controller 17 instructs to end the sterilization step, which is SIP, of the aseptic water tank 25.

A sterilizer is passed through the flow path extending from the outlet of the aseptic water tank 25 to the filling part chamber 3, and SIP of the flow path extending from the outlet of the aseptic water tank 25 to the filling part chamber 3 is performed with the sterilizer. After SIP, aseptic water is passed from the aseptic water producing unit 24 to wash the sterilizer away.

The sterilizer includes a compound having a sterilization effect including an organic acid such as peracetic acid and acetic acid, an inorganic acid such as nitric acid, a basic compound such as sodium hydroxide or potassium hydroxide, a compound with bactericidal effects such as hydrogen peroxide, sodium hypochlorite, chlorine dioxide, or ozone. The sterilizer includes water. However, the sterilizer may include one or two or more of alcohols such as methyl alcohol, ethyl alcohol, isopropyl alcohol, normal propyl alcohol and butyl alcohol, ketones such as acetone, methyl ethyl ketone and acetylacetone, and glycol ether, for example. Furthermore, the sterilizer may include an additive agent such as a cationic surfactant, a nonionic surfactant, and a phosphoric acid compound.

Although the present invention is configured as described above, the present invention is not limited to the embodiment described above, and various modifications can be made within the scope of the spirit of the present invention. The container to be filled with a drink by the drink filling apparatus is not limited to a bottle-shaped container but can be a container of any shape, such as a cup-shaped container, a tray-shaped container or a can-shaped container. The material of the container is not limited to plastics but can be any material such as a composite of paper and plastic, glass, or metal.

REFERENCE SIGNS LIST

2 filling machine
6 upstream-side feedback path
7 drink supply piping
7a upstream-side piping section
7b downstream-side piping section
10 temperature sensor
17 controller
18 heating sterilization part
24 aseptic water producing unit
26 carbonating piping section

The invention claimed is:

1. A method of sterilizing a drink filling apparatus that includes drink supply piping that feeds a drink into a filling machine through a heating sterilization part, passing a heated liquid or heated steam through the drink supply piping to sterilize the drink supply piping during a sterilization step, detecting a plurality of temperatures of the drink supply piping at a plurality of positions by a plurality of temperature sensors at predetermined time intervals, selecting only a lowest temperature from the detected temperatures, calculating an F value for only the selected lowest temperature, integrating the calculated F value, and ending the sterilization step when the integrated F value reaches a target value indicative of a sufficient application of the heated liquid or the heated steam at a temperature and for a time to achieve sterilization, wherein wherein the F value is calculated according to the following formula:

$$F = \int_{t_0}^{t_1} 10^{(T-121.1)/10} dt \qquad \text{[Formula 1]}$$

where T denotes an arbitrary sterilization temperature (° C.), $10^{(T-121.1)/10}$ represents a fatality rate at an arbitrary temperature T and corresponds to a heating duration (in minutes) at 121.1° C., which is a reference temperature, and 10 denotes a Z value (° C.).

2. The method of sterilizing a drink filling apparatus according to claim 1, wherein an upstream-side feedback path is provided for an upstream-side piping section of the drink supply piping that passes through the heating sterilization part to form an upstream-side circulation path, the heated liquid or heated steam is passed through the upstream-side circulation path, temperatures of the upstream-side piping section at a plurality of positions are detected at predetermined time intervals, a lowest temperature is selected from the detected temperatures, an F value is calculated for the selected lowest temperature, the calculated F value is integrated, and a sterilization step of the upstream-side piping section is ended when the integrated F value reaches a target value.

3. The method of sterilizing a drink filling apparatus according to claim 1, wherein the heated liquid or heated steam is passed through a downstream-side piping section of the drink supply piping that extends from a point downstream of an upstream-side piping section of the drink supply piping that passes through the heating sterilization part to an interior of a filling machine via an aseptic surge tank and a filling machine tank, temperatures of the downstream-side piping section at a plurality of positions are detected at predetermined time intervals, a lowest temperature is selected from the detected temperatures, an F value is calculated for the selected lowest temperature, the calculated F value is integrated, and a sterilization step of the downstream-side piping section is ended when the integrated F value reaches a target value.

4. The method of sterilizing a drink filling apparatus according to claim 3, wherein the heated liquid or heated steam is passed through the aseptic surge tank of the downstream-side piping section, temperatures of the aseptic surge tank at a plurality of positions are detected at predetermined time intervals, a lowest temperature is selected from the detected temperatures, an F value is calculated for the selected lowest temperature, the calculated F value is integrated, and a sterilization step of the aseptic surge tank is ended when the integrated F value reaches a target value.

5. The method of sterilizing a drink filling apparatus according to claim 3, wherein the heated liquid or heated steam is passed through a filling piping section of the downstream-side piping section that extends to the interior of the filling machine via the filling machine tank, temperatures of the filling piping section at a plurality of positions are detected at predetermined time intervals, a lowest temperature is selected from the detected temperatures, an F value is calculated for the selected lowest temperature, the calculated F value is integrated, and a sterilization step of the filling piping section is ended when the integrated F value reaches a target value.

6. The method of sterilizing a drink filling apparatus according to claim 3, wherein the heated liquid or heated steam is passed through a carbonating piping section between the aseptic surge tank and the filling machine tank of the downstream-side piping section, the carbonating piping section including a carbonating unit and a carbonated drink surge tank, temperatures of the carbonating piping section at a plurality of positions are detected at predetermined time intervals, a lowest temperature is selected from the detected temperatures, an F value is calculated for the selected lowest temperature, the calculated F value is integrated, and a sterilization step of the carbonating piping section is ended when the integrated F value reaches a target value.

* * * * *